US012005272B1

(12) United States Patent
Crowley

(10) Patent No.: US 12,005,272 B1
(45) Date of Patent: Jun. 11, 2024

(54) DEVICES TO HOLD RADIATION PROBES DURING ADMINISTRATION OF A NUCLEAR MEDICATION

(71) Applicant: James R Crowley, Roanoke, VA (US)

(72) Inventor: James R Crowley, Roanoke, VA (US)

(73) Assignee: Carilion Clinic, Roanoke, VA (US)

( * ) Notice: Subject to any disclaimer, the term of this patent is extended or adjusted under 35 U.S.C. 154(b) by 129 days.

(21) Appl. No.: 17/175,805

(22) Filed: Feb. 15, 2021

Related U.S. Application Data

(60) Provisional application No. 62/976,288, filed on Feb. 13, 2020, provisional application No. 62/976,285, filed on Feb. 13, 2020.

(51) Int. Cl.
*A61N 5/10* (2006.01)
*G01T 1/18* (2006.01)

(52) U.S. Cl.
CPC ......... *A61N 5/1071* (2013.01); *A61N 5/1001* (2013.01); *G01T 1/18* (2013.01); *A61N 2005/1021* (2013.01)

(58) Field of Classification Search
CPC .............. G01T 1/18; A61N 2005/1021; A61N 5/1001; A61N 5/1071
See application file for complete search history.

(56) References Cited

U.S. PATENT DOCUMENTS

| 6,217,503 | B1 | | 4/2001 | Wineberger | |
|---|---|---|---|---|---|
| 8,317,674 | B2 | * | 11/2012 | Quirico | A61M 5/14 |
| | | | | | 600/5 |
| 9,108,047 | B2 | * | 8/2015 | Agamaite | A61M 3/00 |
| 9,114,203 | B2 | * | 8/2015 | Quirico | A61M 5/14 |
| 9,123,449 | B2 | * | 9/2015 | Quirico | A61M 5/365 |
| 9,326,742 | B2 | * | 5/2016 | Hirschman | G21G 4/08 |
| 11,794,034 | B1 | | 10/2023 | Crowley | |
| 11,865,304 | B1 | | 1/2024 | Crowley | |
| 2006/0151048 | A1 | * | 7/2006 | Tochon-Danguy | G21F 5/015 |
| | | | | | 141/27 |
| 2008/0242915 | A1 | | 10/2008 | Jackson | |
| 2011/0124948 | A1 | | 5/2011 | Yokell | |
| 2011/0178359 | A1 | | 7/2011 | Hirschman | |
| 2012/0305800 | A1 | | 12/2012 | Mayfield | |
| 2014/0296611 | A1 | | 10/2014 | Schwartz | |
| 2015/0327941 | A1 | | 11/2015 | Haynes | |
| 2018/0345037 | A1 | | 12/2018 | Starz | |
| 2020/0016284 | A1 | * | 1/2020 | Schimmoeller | A61N 5/1007 |
| 2021/0268187 | A1 | | 9/2021 | Gertsenchtein | |

* cited by examiner

*Primary Examiner* — Christine H Matthews
*Assistant Examiner* — Marc D. Honrath
(74) *Attorney, Agent, or Firm* — Rhodes IP PLC; Christopher R Rhodes

(57) ABSTRACT

Certain configurations are described of devices that can receive and retain a radiation measuring device during administration of a nuclear medication. In some instances, the radiation measuring device can measure radiation levels being delivered through an intravenous line positioned within the device and connected to a patient. Methods and systems using the devices are also described.

20 Claims, 5 Drawing Sheets

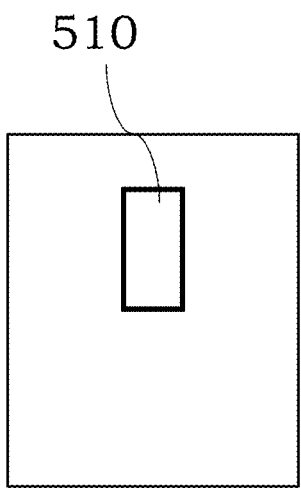
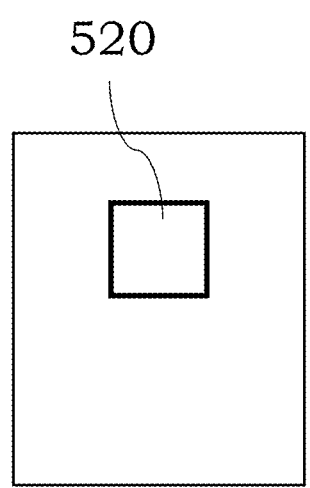
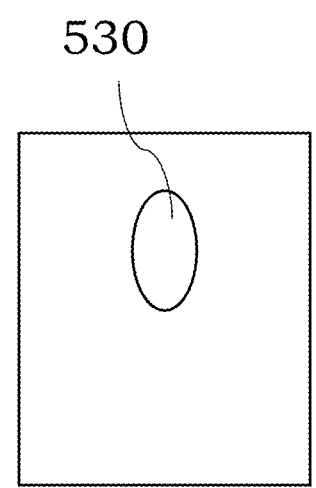
FIG. 5A  FIG. 5B  FIG. 5C
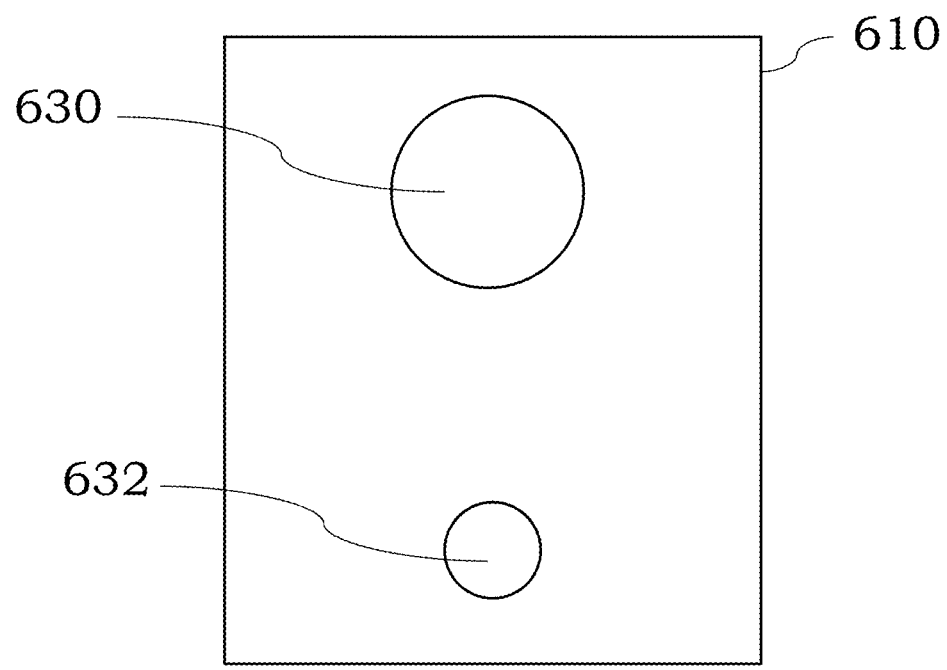
FIG. 6

DEVICES TO HOLD RADIATION PROBES DURING ADMINISTRATION OF A NUCLEAR MEDICATION

PRIORITY APPLICATION

This application is related to, and claims priority to and the benefit of, U.S. Provisional Application No. 62/976,285 filed on Feb. 13, 2020 and U.S. Provisional Application No. 62/976,288 filed on Feb. 13, 2020. The entire disclosure of each of these applications is hereby incorporated herein by reference.

TECHNOLOGICAL FIELD

Certain embodiments described herein are directed to devices and methods that can retain a radiation probe during administration of a nuclear medication.

BACKGROUND

Delivery of nuclear medications is often an imprecise process. The nuclear medication used can also undesirably expose staff members to radiation doses.

SUMMARY

Certain specific configurations and aspects of a device that can retain a radiation probe, e.g., a radiation probe measuring head, during administration of a radiotherapeutic material or nuclear medication are described below. The specific configurations that are described are provided merely for illustration and are not intended to limit the scope of the claims.

In an aspect, a device configured to receive and retain a radiation probe during administration of a nuclear medication is provided. In certain configurations, the device comprises a substrate comprising an aperture configured to receive and retain the radiation probe at a first surface of the substrate. In some embodiments, the substrate is configured to receive and retain a fluid line at a second surface of the substrate. In other embodiments, the aperture is configured to position the received radiation probe to measure radioactivity of the nuclear medication passing through the received fluid line during administration of the nuclear medication. In some instances, the substrate can be configured to provide a constant geometry for accurate measurements to more accurately understand dose delivery. In certain embodiments, the device can provide additional distance between the nuclear medication and any staff members to reduce exposure to staff.

In certain embodiments, the aperture is sized and arranged to receive the radiation probe from a Geiger counter. In other embodiments, the aperture is sized and arranged to receive and retain the entire radiation probe of the Geiger counter. In some configurations, the aperture is sized and arranged to receive and retain a head of the radiation probe of the Geiger counter. In certain embodiments, the second surface comprises a slot configured to receive and retain the fluid line. In other embodiments, the slot is configured to position the received and retained fluid line transversely so the received and retained fluid line passes under a center of the received radiation probe.

In certain embodiments, the substrate comprises a low Z material. Examples of low Z materials include, but are not limited to, an acrylic, a plastic, a rubber, wood, or other non-metallic materials. If desired, the substrate can be filled with a liquid, e.g., water, or particles suspended in a liquid.

In certain configurations, the device may comprise a handle coupled to the substrate. For example, the handle can be configured to receive and retain a reservoir comprising the nuclear medication and/or can be used to move the substrate from site to site.

In another aspect, a device can be configured to receive a radiation measuring probe on one surface and fluid tubing on another surface. For example, the device can be configured to maintain a constant geometry for accurate measurements during delivery of a nuclear medication through the fluid tubing. The device may also permit lesser exposure of staff members to the nuclear medication during administration.

In another aspect, a system for administering a nuclear medication to a subject is provided. In certain embodiments, the system comprises a radiation measurement device comprising a radiation probe. The system can also include a device configured to receive and retain the radiation probe during administration of the nuclear medication, the device comprising a substrate comprising an aperture configured to receive and retain the radiation probe at a first surface of the substrate, wherein the substrate is configured to receive and retain a fluid line at a second surface of the substrate, and wherein the aperture is configured to position the received radiation probe to measure radioactivity of the nuclear medication passing through the received fluid line during administration of the nuclear medication.

In certain embodiments, the radiation measurement device is a Geiger counter. In other embodiments, the second surface comprises a slot configured to receive and retain the fluid line, wherein the slot is configured to position the received and retained fluid line transversely so the received and retained fluid line passes under a center of the received radiation probe. In some embodiments, the substrate used in the system comprises a low Z material. Examples of low Z materials include, but are not limited to, an acrylic, a plastic, a rubber, wood, or other non-metallic materials. If desired, the substrate can be filled with a liquid, e.g., water, or particles suspended in a liquid. In certain examples, the substrate comprises a handle configured to receive and retain a reservoir comprising the nuclear medication.

In another aspect, a method of administering a nuclear medication to a subject comprises placing a radiation probe in a device configured to receive and retain the radiation probe during administration of the nuclear medication, and placing a fluid line at a second surface of the substrate. In certain embodiments, the device comprises a substrate comprising an aperture configured to receive and retain the radiation probe at a first surface of the substrate. For example, the aperture can be configured to position the received radiation probe to measure radioactivity of the nuclear medication passing through the received fluid line during administration of the nuclear medication.

In certain embodiments, the method comprises configuring the second surface with a slot to receive and retain the fluid line. In other embodiments, the method comprises configuring the aperture to receive and retain a head of the radiation probe of a Geiger counter. In additional embodiments, the method comprises configuring the substrate to shield a user from radiation as the radiation probe is placed into the aperture. In some embodiments, the method comprises configuring the substrate with a handle to receive and retain a reservoir comprising the nuclear medication.

In another aspect, a kit comprises a device configured to receive and retain a radiation probe during administration of a nuclear medication, and written or electronic instructions for using the device to administer the nuclear medication. For example, the device can include a substrate comprising an aperture configured to receive and retain the radiation probe at a first surface of the substrate, wherein the substrate is configured to receive and retain a fluid line at a second surface of the substrate, and wherein the aperture is configured to position the received radiation probe to measure radioactivity of the nuclear medication passing through the received fluid line during administration of the nuclear medication.

In certain embodiments, the kit can also include a reservoir comprising the nuclear medication. In other embodiments, the kit can also include a fluid line. In some embodiments, the kit can include a radiation measuring device, e.g., a Geiger counter comprising the radiation probe.

In another aspect, a method comprises monitoring delivery of a nuclear medication using the device described herein. For example, the method can include monitoring radiation levels and notifying a user when the delivery of the nuclear medication is complete. In some embodiments, the method can include notifying a user when the rate of radioactivity reaches a programmed level which can be based on the manufacturers delivery instruction. In other instances, the method can include recording the treatment in an electronic medical record in an automated manner.

In an additional aspect, a method of monitoring infusion of a nuclear medication to a patient is described. In some configurations, the method comprises measuring radiation levels of a nuclear medication passing through an intravenous line connected to the patient using a device configured to receive and retain a radiation probe during infusion of a nuclear medication, the device comprising a substrate comprising an aperture configured to receive and retain the radiation probe at a first surface of the substrate, wherein the substrate is configured to receive and retain the intravenous line at a second surface of the substrate, and wherein the aperture is configured to position the received radiation probe to measure radiation levels of the nuclear medication passing through the received intravenous line during infusion of the nuclear medication. In certain embodiments, the method can include generating an alert when the measured radiation levels have reached a selected counts per hour.

In another aspect, a method of treating a patient using a nuclear medication is disclosed. In certain embodiments, the method comprises counting radiation of the nuclear medication passing through an intravenous line connected to the patient using a device configured to receive and retain a radiation probe during infusion of a nuclear medication, the device comprising a substrate comprising an aperture configured to receive and retain the radiation probe at a first surface of the substrate, wherein the substrate is configured to receive and retain the intravenous line at a second surface of the substrate, and wherein the aperture is configured to position the received radiation probe to measure radiation levels of the nuclear medication passing through the received intravenous line during infusion of the nuclear medication. The method can also include discontinuing infusion of the nuclear medication after a selected counts per hour of the radiation are measured. In certain instances, the method can include generating an alert when the selected counts per hour of the radiation are measured.

Additional aspect, embodiments, configurations and examples are described in more detail below.

BRIEF DESCRIPTION OF THE SEVERAL VIEWS OF THE DRAWINGS

FIGS. 5A, 5B and 5C show different aperture shapes, in accordance with certain embodiments;

FIG. 6 is an illustration of a device including two separate apertures, in accordance with some embodiments;

DETAILED DESCRIPTION

In the administration of nuclear medication being given to a patient, continuous measurements of the radiation level of that medication are typically measured/monitored for the full duration of delivery. Measurement of radioactivity can be performed at a location mid-way along the intravenous (IV) tubing, between the IV bag, or syringe, containing said nuclear medication and the entry point on the patient. Typical past practice has been to hold a radiation measuring device, such as a Geiger counter probe, over the IV tubing at a chosen but consistent distance for the duration of the administration of the medication. One key difficulty with this method of measurement is the ability and skill of the attending technician to hold the Geiger counter probe in a steady, consistent and repeatable manner for the full duration of the medication administration. This duration can typically last for approximately 10 minutes or more, but the duration can vary widely. Resulting measurements can vary widely using this method.

In certain embodiments, the devices described herein can provide a controlled positioning between the fluid line and the radiation probe for more consistent measurements and delivery of a nuclear medication. The exact radiation probe used can vary depending on the particular nuclear medication used with typical radiation probes being designed to measure one or more of alpha, beta and gamma radiation. For example, a Geiger counter probe can be used to measure radioactivity levels of a nuclear medication being delivered to a patient. Other devices that can be used to measure radiation include, but are not limited to, a PIN diode, a Geiger Mueller (G-M) tube, a gas filled detector, a scintillator or a solid state detector. As discussed in more detail below, the substrates described herein can be configured to receive and retain a radiation probe of the radiation measurement device and hold the probe a fixed and constant distance from a fluid line comprising the nuclear medication. If desired, the device can be used in combination with a system to deliver a nuclear medication in an automated manner to a patient. Illustrative systems are described, for example, in U.S. Provisional Application No. 62/976,288 filed on Feb. 13, 2020.

Figure 1:
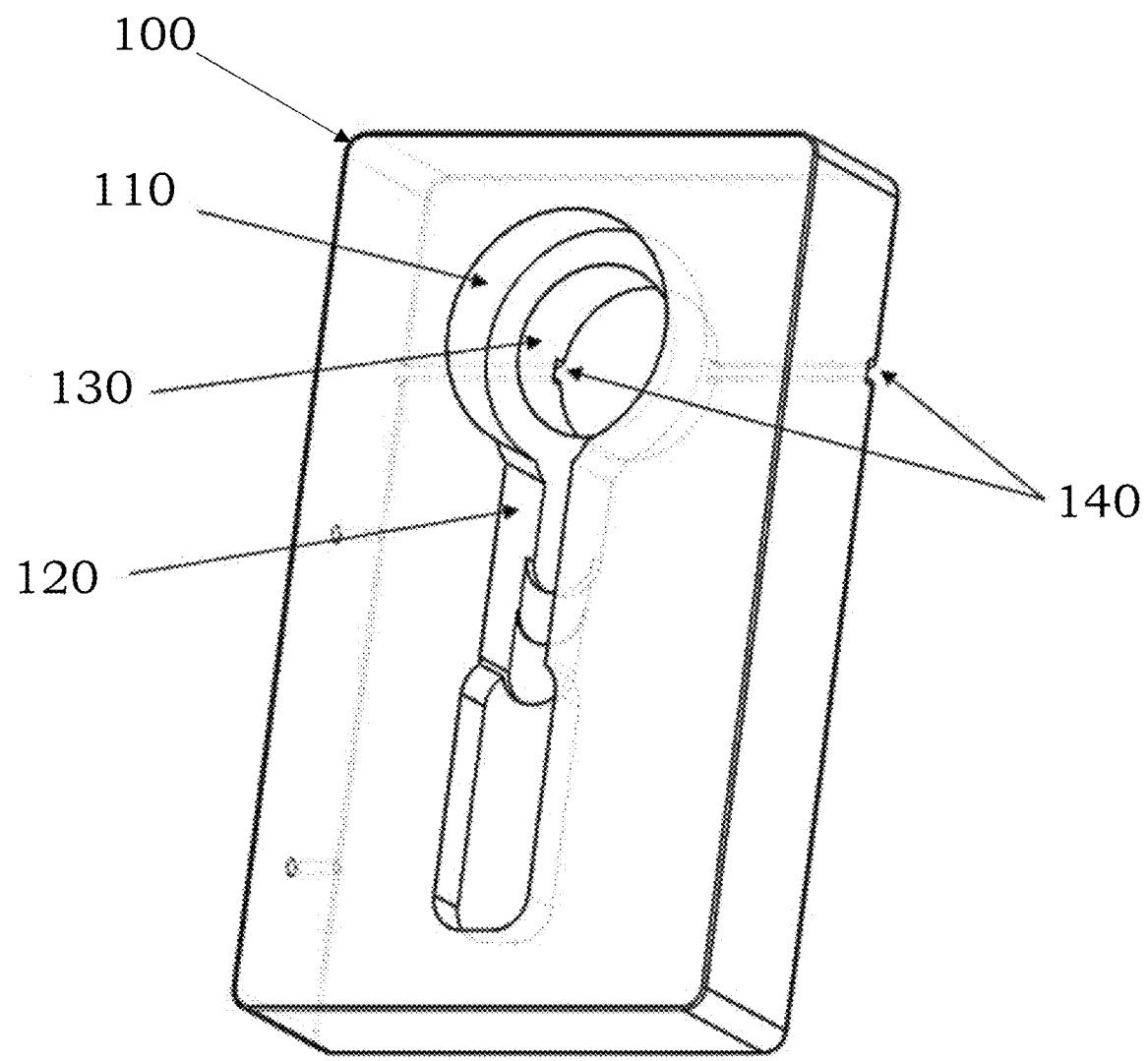
FIG. 1 is an illustration of a device that can be used to deliver a nuclear medication, in accordance with some embodiments.
Figure 2:
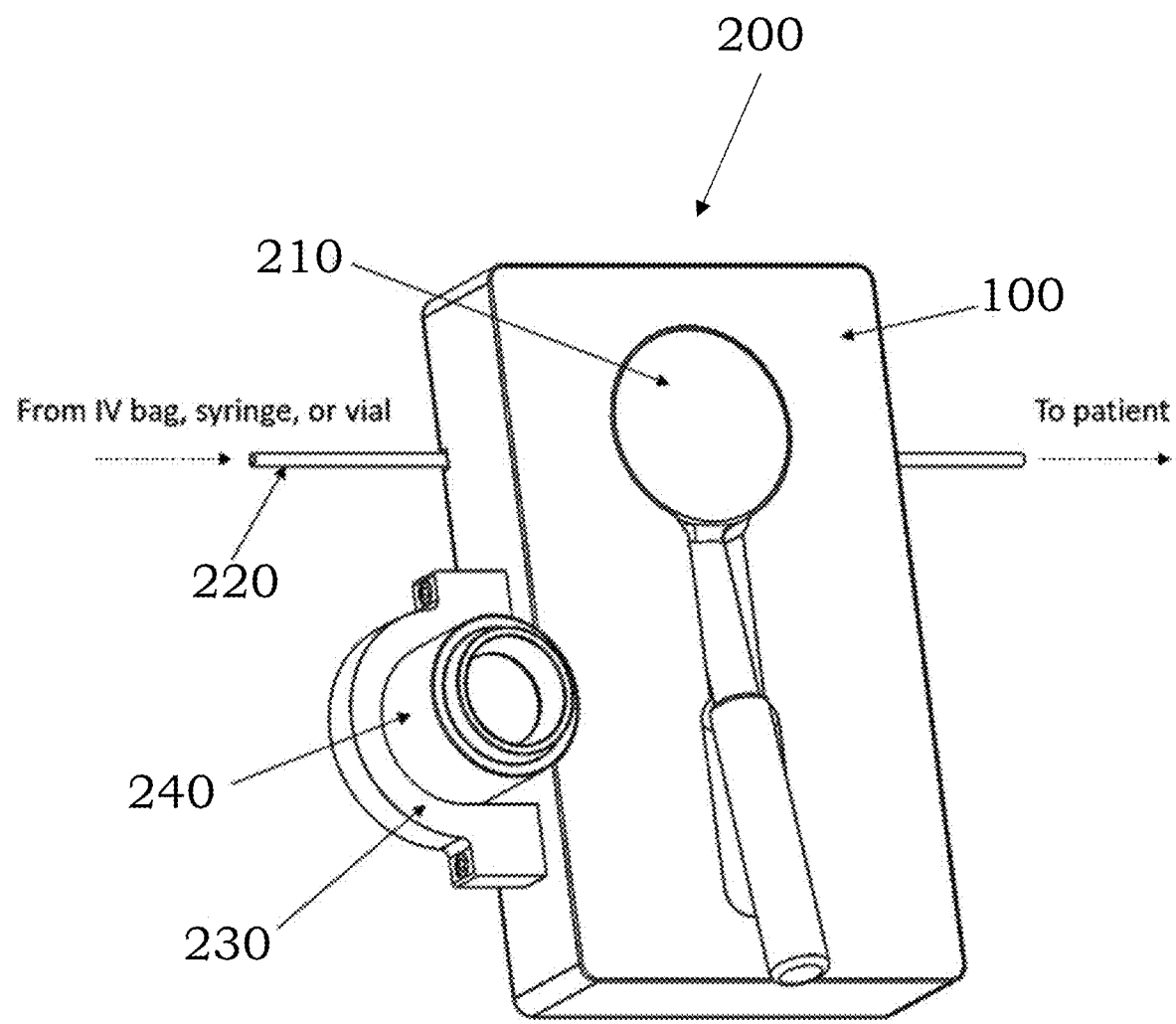
FIG. 2 is another illustration of a device that can be used to deliver a nuclear medication, in accordance with some embodiments.

Referring to FIGS. 1 and 2, a substrate 100 is shown that comprises an aperture 110 configured to receive radiation measuring device, such as a Geiger counter probe 210, for the measurement of radioactive medication being delivered through an IV tube. The device is comprised of the substrate 100, made from an appropriate material, which has appropriately-shaped and closely dimensioned pockets or apertures 110, 120. For example, the aperture 110 can receive a head of the radiation probe and the aperture 120 can receive a handle of the radiation probe. The apertures 110, 120 can be sized and arranged to securely and/or uniquely fit a particular type of radiation probe, e.g., to securely and uniquely fit to a typical Geiger counter probe 210. These apertures 110, 120 are located on the top of the substrate 100. The dimensions and shape of the apertures are such that the Geiger counter probe 210 will fit securely and precisely into the block substrate 100, without excessive clearance. For example, the approximate overall dimensions of one configuration of the substrate 100 are 2 inches in thickness, 6 inches wide (side-to-side) and 10 inches in length. The substrate 100 may be hollow or may be solid or may be filled with a liquid or other material, e.g., radiation absorbing particles.

In certain embodiments, the radiation measurement axis is typically parallel to the thickness dimension of the substrate 100. In this configuration, a slot 140 is located on the bottom face of the substrate 100. The slot dimensions are selected such that the IV tubing 220 will fit into, and be retained by, the slot 140 by way of a friction fit. The slot 140 extends from one side of the substrate 100 to the opposite side, at a transverse location such that the IV tubing 220 passes directly under the center of the Geiger counter probe 210 measuring face. Also, the apertures 110, 120 form a through hole or open space 130 that passes all the way through the substrate, from top to bottom. For example, the hole 130 may be approximately 2 inches in diameter, located concentric to the measurement axis of the Geiger counter probe 210, and perpendicular to the measurement face of the Geiger counter probe 210. This hole 130 allows the Geiger counter probe 210 to "see" or "look" at the aforementioned IV tubing 220 positioned in the slot 140. This aperture 130 results in only airspace between the measurement face of the Geiger counter probe 210 and the IV tubing 220. The distance between the face of the probe 210 and the tubing 220 remains constant during administration of the nuclear medicine.

In certain embodiments, the substrate can include a handle 230 to facilitate carrying and positioning of the device 200. The handle 230 also serves to secure the position of a transportation container 240 (sometimes also referred to as a "pig") for the vial containing nuclear medication. The handle 230 can have many different shapes including circular, rectangular, square, etc.

In certain embodiments, the exact material used to produce the substrate 100 can vary. For example, acrylic plastic material is one good candidate choice for the substrate 100 due to a number of desirable properties. Acrylic is relatively inexpensive, is lightweight and can provide some measure of shielding and attenuation of the radiation to the nearby environment. These features can serve to allow the radiation measuring device to measure only that radiation within the cylindrical airspace being emitted from the medication and passing through the IV tubing 220 which crosses the "measurement" aperture 130.

In certain embodiments, the substrate 100 may comprise a low Z material. Without wishing to be bound by any one configuration, a low Z material can include a plastic, a non-metal, rubber, wood, water or liquids or other materials. In some embodiments, the low Z material can include a polymeric material that optionally can absorb radiation that is emitted by beta decay, gamma decay or both. In some embodiments, the substrate 100 can include one or more thermoplastic materials or thermosetting materials. For example, suitable materials that can be used to produce the substrate 100 include, but are not limited to, an acrylic, an acrylonitrile butadiene styrene, a nylon, a polylactic acid, a polybenzimidazole, a polycarbonate, a polyether sulfone, a polyether ether ketone, a polyetherimide, a polyethylene, a polypropylene, a polyphenylene oxide, a polyphenylene sulfide, a polystyrene, a polyvinyl chloride, a polyvinyledene fluoride, a polytetrafluorethylene, a polyurethane, a polyester, an epoxy or epoxide material, a polyimide, a maleimide, a bismaleimide, a cyanate ester, a vinyl ester or other materials. In some embodiments, the substrate may include an acrylate, a polyacrylate, a polyolefin, and a co-polymer thereof. In certain embodiments, the substrate 100 can include a homopolymer of acrylic acid or an acrylic acid that has been cross-linked with an ether or other material. The material of the substrate 100 is typically rigid, though it may be flexible or flexible at least to some degree if desired. In some embodiments, the substrate 100 can include poly(methylmethacrylate) or another form of an acrylic glass. The substrate 100 may be colored, colorless, transparent or opaque as desired. The substrate 100 can be solid, hollow or include internal regions that are hollow. If desired, the hollow regions can be filled with a liquid, e.g., water, particle that can absorb radiation or other materials.

Figure 3:
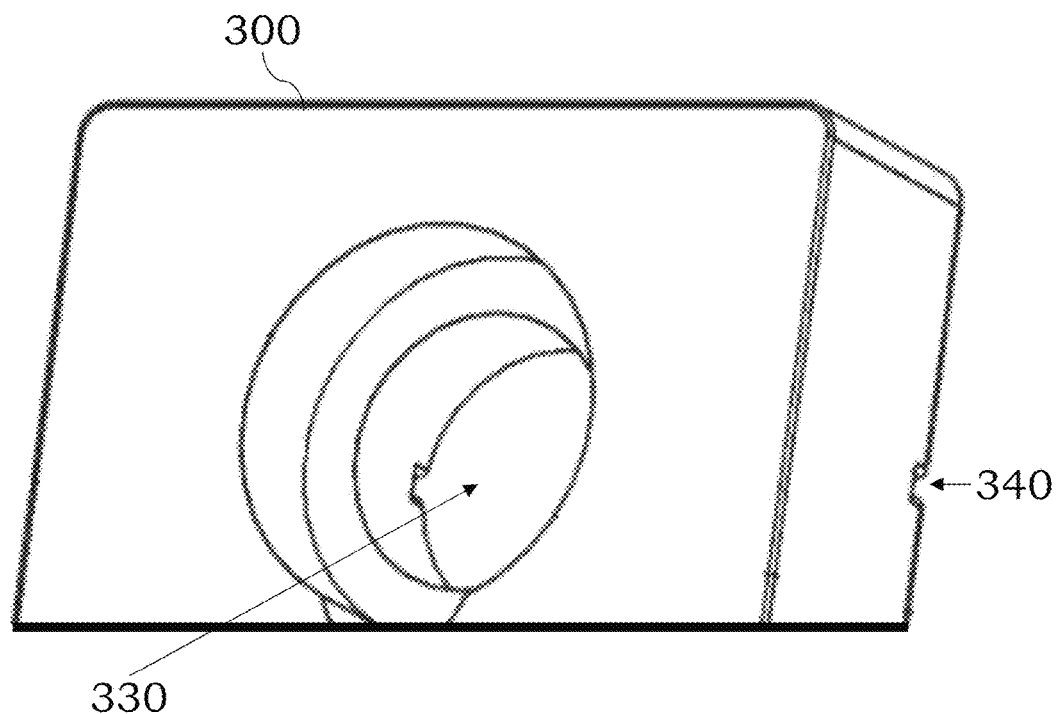
FIG. 3 is an additional illustration of a device that can be used to deliver a nuclear medication, in accordance with some embodiments.

In certain embodiments, the substrate need not be configured to receive an entire radiation probe. For example and referring to FIG. 3, a substrate 300 comprises a generally solid block with an aperture 330 that can receive only a head of a radiation probe, e.g., only a head of a Geiger counter probe (not shown). The head of the radiation probe can be placed into the aperture 330 above a slot 340 configured to receive a fluid line including the nuclear medication. The remaining portion of the radiation probe is positioned outside of the aperture 330. While not shown, the aperture 330 could include a slot at a lower end to permit a handle of the Geiger counter probe to exit the substrate 300 after placement of the head of the Geiger counter probe into the substrate 100. The substrate 100 can include many different overall shapes including rectangular, square, triangular, circular, elliptical and other shapes. The substrate 100 shape can be asymmetric or symmetric as desired.

Figure 4:
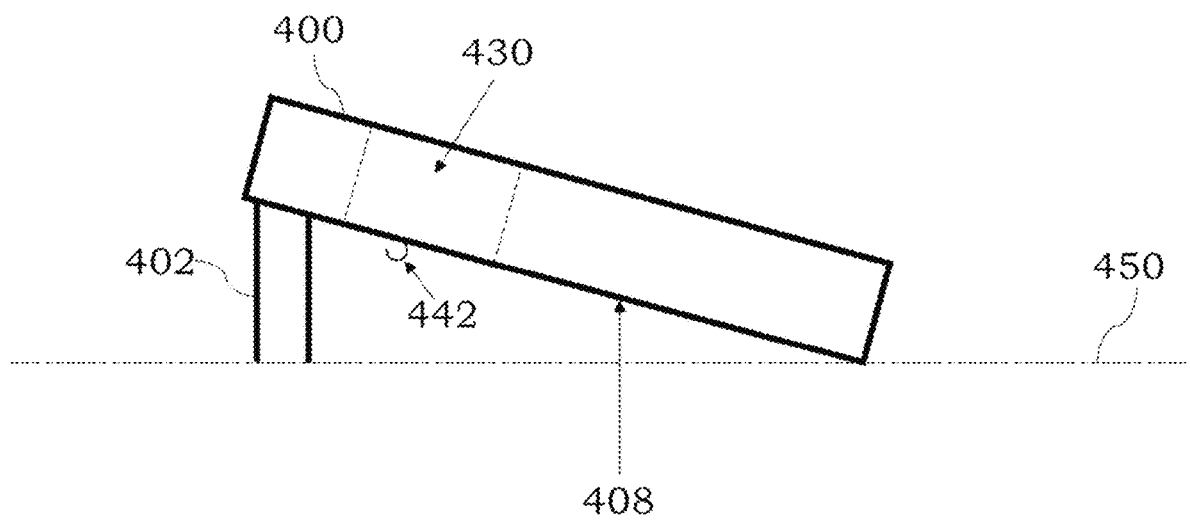
FIG. 4 is an illustration of a non-planar device that can be used to deliver a nuclear medication, in accordance with some embodiments.

In certain configurations, the substrate may not include a slot but could include other features to retain a fluid line in position during use of the device to deliver a nuclear medication. For example, in some instances the substrate can generally be planar and include a slot such that the substrate and received fluid line can be placed flat on a hospital table tray during use. In other instances, some surface or areas of the substrate may be non-planar. Referring to FIG. 4 a substrate 400 is shown that comprises a non-planar surface 408, relative to planar surface 450, which can be the surface of a tray table or other table that the substrate 400 rests on during use. The substrate 400 includes an arm or extension 402 that positions the surface 408 at an angle with respect to the surface 450. The substrate 400 includes an aperture 430 that can receive a radiation probe and a hook 442 that can receive a fluid line. While not shown, a second hook is typically positioned an a second side of the substrate 400 to keep the fluid line elevated in use of the substrate 400. For example, the fluid line can be placed into the hooks to hold the fluid line a fixed distance from a head of the probe placed in the aperture 430. The exact distance between the placed probe head and the fluid line is not critical but desirably remains constant during administration of the nuclear medicine to the patient. The extension 402 may be fixed, foldable or adjustable to position the surface 408 at a desired angle with respect to the surface 450. If desired, the substrates described herein can include non-skid features to increase friction between the substrate and any underlying table or surface. The non-skid features can reduce the likelihood of movement of the substrate during administration of the nuclear medicine. The non-skid features can be added to a surface of the substrate or can be part of the materials used to produce the substrates described herein.

In certain embodiments, the exact shape of the aperture of the device may vary depending on the overall shape of the radiation probe. While not required in all instances, the aperture shape can be designed or selected to mirror the shape of the head of the radiation probe. While FIGS. 1 and 2 show a circular aperture shape, this shape is not required. For example, FIG. 5A shows a rectangular aperture 510, FIG. 5B shows a square aperture 520 and FIG. 5C shows an elliptical aperture 530. If desired, a gasket, seal or other means may be present around outer edges of the apertures to provide a seal between a face of the radiation probe and the substrate.

In certain embodiments, the devices described herein may include more than a single aperture. For example and referring to FIG. 6, a substrate 610 is shown with a first aperture 630 and a second aperture 632. The apertures 630, 632 are sized differently and can accept radiation probes of different sizes. Three, four, five or more different apertures may be present if desired. The different apertures need not have the same shape or dimensions. While not shown, a slot may be present under each aperture 630, 632 so any fluid line placed into the substrate 610 runs generally transverse to the inserted radiation probe. Alternatively, a single slot can be placed lengthwise, e.g., parallel to the long axis, such that the single slot underlies both apertures 630, 632. In such configurations, different radiation measuring devices may be placed into the different apertures 630, 632 and can be used to measure different types of radiation simultaneously.

In some embodiments, the devices described herein can be used in a method to administer a nuclear medication to a subject. The process can include placing a radiation probe in a device configured to receive and retain the radiation probe during administration of the nuclear medication, the device comprising a substrate comprising an aperture configured to receive and retain the radiation probe at a first surface of the substrate. The process can also include placing a fluid line at a second surface of the substrate, wherein the second surface of the substrate is configured to receive and retain the fluid line, and wherein the aperture is configured to position the received radiation probe to measure radioactivity of the nuclear medication passing through the received fluid line during administration of the nuclear medication. If desired, treatment can be discontinued after a certain radiation dose has been provided to the patient.

In certain embodiments, the method can include configuring the second surface with a slot to receive and retain the fluid line. An air space can be between the tubing and the radiation probe. In certain embodiments, the aperture is configured to receive and retain a head of the radiation probe of a Geiger counter. The substrate can be configured to shield a user from radiation as the radiation probe is placed into the aperture. If desired, the substrate can include a handle to receive and retain a reservoir comprising the nuclear medication.

Figure 7:
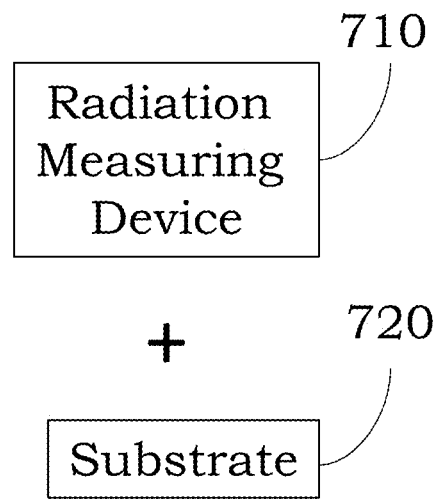
FIG. 7 is a block diagram of a system including a radiation measuring device and a substrate, in accordance with certain embodiments.

In certain embodiments, the substrate may be part of a system that includes a radiation measurement device. A block diagram is shown in FIG. 7 where a system includes a radiation measuring device 710 and a substrate 720. The system may include written or electronic instructions of using the substrate 720 with the radiation measuring device 710 during administration of a nuclear medicine to a patient.

Figure 8:
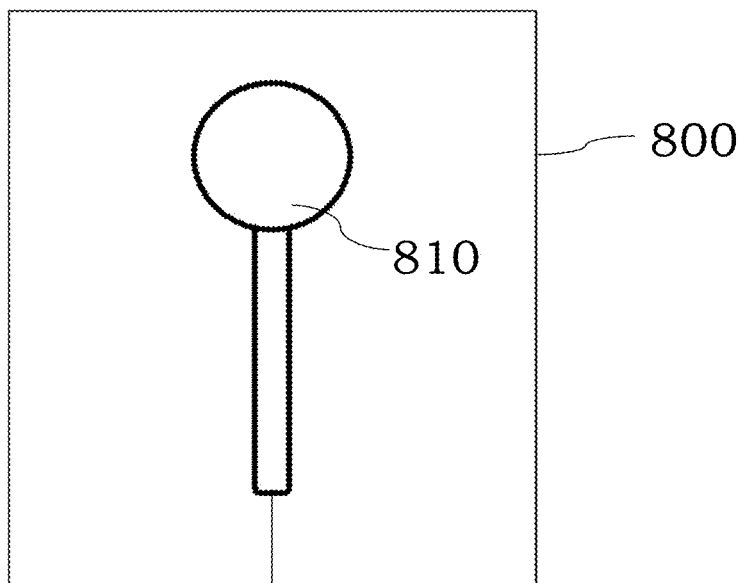
FIG. 8 is a block diagram of another system that can be used to deliver a nuclear medication to a patient, in accordance with certain embodiments.
Figure 8:
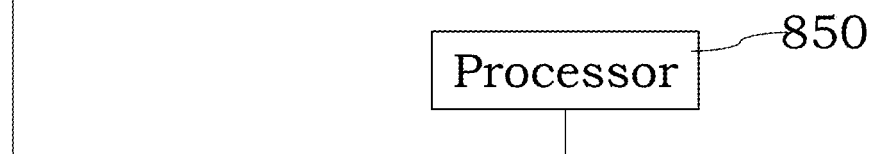

Another illustration of a system is shown in FIG. 8, where the radiation measuring device 810 has been inserted into the substrate 800. The radiation measuring device 810 is electrically coupled to a processor 850. If desired, the processor 850 can implement a software routine to administer the nuclear medication to a patient. In some configurations, a simple software program to notify or alarm when the delivery has completed, e.g., when the patient has received a pre-selected level of nuclear medication, and can an output a record into the electronic medical record of the patient. The processor 850 can also generally control the system if desired. For example, the systems described herein may be controlled using one or more processors, which can be part of the radiation measuring device or present as a separate system through an associated device, e.g., computer, laptop, mobile device, etc. For example, the processor can be used to determine the radiation levels, determine if treatment should continue, can write a treatment record to an electronic medical record, and otherwise control other parameters of the process and system. Such processes may be performed automatically by the processor without the need for user intervention or a user may enter parameters through a user interface. In certain configurations, the processor may be present in one or more computer systems and/or common hardware circuitry including, for example, a microprocessor and/or suitable software for operating the system, e.g., to measure the radiation, etc. The processor can be integral to the system or may be present on one or more accessory boards, printed circuit boards or computers electrically coupled to the components of the in-line system. The processor is typically electrically coupled to one or more memory units to receive data from the other components of the system and permit adjustment of the various system parameters as needed or desired. The processor may be part of a general-purpose computer such as those based on Unix, Intel PENTIUM-type processor, Intel Core™ processors, Intel Xeon™ processors, AMD Ryzen™ processors, AMD Athlon™ processors, AMD FX™ processors, Motorola PowerPC, Sun UltraSPARC, Hewlett-Packard PA-RISC processors, Apple-designed processors including Apple A14 Bionic processor, A13 Bionic processor, A12 processor, Apple A11 processor and others or any other type of processor. One or more of any type computer system may be used according to various embodiments of the technology. Further, the system may be connected to a single computer or may be distributed among a plurality of computers attached by a communications network. If desired, different components of the in-line system may be controlled by a respective processor or computer that is separate from a processor or computer used to control other components of the in-line system. It should be appreciated that other functions, including network communication, can be performed and the technology is not limited to having any particular function or set of functions. Various aspects may be implemented as specialized software executing in a general-purpose computer system. The computer system may include a processor connected to one or more memory devices, such as a disk drive, memory, or other device for storing data. Memory is typically used for storing radiation measurements, treatment routines, electronic medical records and other values. Components of the computer system may be coupled by an interconnection device, which may include one or more buses (e.g., between components that are integrated within a same machine) and/or a network (e.g., between components that reside on separate discrete machines). The interconnection device provides for communications (e.g., signals, data, instructions) to be exchanged between components of the system. The computer system typically can receive and/or issue commands within a processing time, e.g., a few milliseconds, a few microseconds or less, to permit rapid control of the system. The processor typically is electrically coupled to a power source which can, for example, be a direct current source, an alternating current source, a battery, a solar cell, a fuel cell or other power sources or combinations of power sources. The power source can be shared by the other components of the system. The system may also include one or more input devices, for example, a keyboard, mouse, trackball, microphone, touch screen, manual switch (e.g., override switch) and one or more output devices, for example, a printing device, display screen, speaker. In addition, the system may contain one or more communication interfaces that connect the computer system to a communication network (in addition or as an alternative to the interconnection device). The system may also include suitable circuitry to convert signals received from the various electrical devices present in the systems. Such circuitry can be present on a printed circuit board or may be present on a separate board or device that is electrically coupled to the printed circuit board through a suitable interface, e.g., a serial ATA interface, ISA interface, PCI interface, a USB interface, a Fibre Channel interface, a Firewire interface, a M.2 connector interface, a PCIE interface, a mSATA interface or the like or through one or more wireless interfaces, e.g., Bluetooth, Wi-Fi, Near Field Communication or other wireless protocols and/or interfaces.

In certain embodiments, the storage system used in the systems described herein typically includes a computer readable and writeable nonvolatile recording medium in which codes of software can be stored that can be used by a program to be executed by the processor or information stored on or in the medium to be processed by the program. The medium may, for example, be a hard disk, solid state drive or flash memory. The program or instructions to be executed by the processor may be located locally or remotely and can be retrieved by the processor by way of an interconnection mechanism, a communication network or other means as desired. Typically, in operation, the processor causes data to be read from the nonvolatile recording medium into another memory that allows for faster access to the information by the processor than does the medium. This memory is typically a volatile, random access memory such as a dynamic random access memory (DRAM) or static memory (SRAM). It may be located in the storage system or in the memory system. The processor generally manipulates the data within the integrated circuit memory and then copies the data to the medium after processing is completed. A variety of mechanisms are known for managing data movement between the medium and the integrated circuit memory element and the technology is not limited thereto. The technology is also not limited to a particular memory system or storage system. In certain embodiments, the system may also include specially-programmed, special-purpose hardware, for example, an application-specific integrated circuit (ASIC), microprocessor units MPU) or a field programmable gate array (FPGA) or combinations thereof. Aspects of the technology may be implemented in software, hardware or firmware, or any combination thereof. Further, such methods, acts, systems, system elements and components thereof may be implemented as part of the systems described above or as an independent component. Although specific systems are described by way of example as one type of system upon which various aspects of the technology may be practiced, it should be appreciated that aspects are not limited to being implemented on the described system. Various aspects may be practiced on one or more systems having a different architecture or components. The system may comprise a general-purpose computer system that is programmable using a high-level computer programming language. The systems may be also implemented using specially programmed, special purpose hardware. In the systems, the processor is typically a commercially available processor such as the well-known microprocessors available from Intel, AMD, Apple and others. Many other processors are also commercially available. Such a processor usually executes an operating system which may be, for example, the Windows 7, Windows 8 or Windows 10 operating systems available from the Microsoft Corporation, MAC OS X, e.g., Snow Leopard, Lion, Mountain Lion, Mojave, High Sierra, El Capitan or other versions available from Apple, the Solaris operating system available from Sun Microsystems, or UNIX or Linux operating systems available from various sources. Many other operating systems may be used, and in certain embodiments a simple set of commands or instructions may function as the operating system.

In certain examples, the processor and operating system may together define a platform for which application programs in high-level programming languages may be written. It should be understood that the technology is not limited to a particular system platform, processor, operating system, or network. Also, it should be apparent to those skilled in the art, given the benefit of this disclosure, that the present technology is not limited to a specific programming language or computer system. Further, it should be appreciated that other appropriate programming languages and other appropriate systems could also be used. In certain examples, the hardware or software can be configured to implement cognitive architecture, neural networks or other suitable implementations. If desired, one or more portions of the computer system may be distributed across one or more computer systems coupled to a communications network. These computer systems also may be general-purpose computer systems. For example, various aspects may be distributed among one or more computer systems configured to provide a service (e.g., servers) to one or more client computers, or to perform an overall task as part of a distributed system. For example, various aspects may be performed on a client-server or multi-tier system that includes components distributed among one or more server systems that perform various functions according to various embodiments. These components may be executable, intermediate (e.g., IL) or interpreted (e.g., Java) code which communicate over a communication network (e.g., the Internet) using a communication protocol (e.g., TCP/IP). It should also be appreciated that the technology is not limited to executing on any particular system or group of systems. Also, it should be appreciated that the technology is not limited to any particular distributed architecture, network, or communication protocol.

In some instances, various embodiments may be programmed using an object-oriented programming language, such as, for example, SQL, SmallTalk, Basic, Java, Javascript, PHP, C++, Ada, Python, iOS/Swift, Ruby on Rails or C #(C-Sharp). Other object-oriented programming languages may also be used. Alternatively, functional, scripting, and/or logical programming languages may be used. Various configurations may be implemented in a non-programmed environment (e.g., documents created in HTML, XML or other format that, when viewed in a window of a browser program, render aspects of a graphical-user interface (GUI) or perform other functions). Certain configurations may be implemented as programmed or non-programmed elements, or any combination thereof. In some instances, the systems may comprise a remote interface such as those present on a mobile device, tablet, laptop computer or other portable devices which can communicate through a wired or wireless interface and permit treatment using the nuclear medication as desired.

In certain examples, the processor may also comprise or have access to a database of information about nuclear medications, radiation levels, treatment times, and other parameters used to treat a patient with a nuclear medicine. For example, specific treatment doses for a particular nuclear medication can be retrieved from the database and used by the system. The instructions stored in the memory can execute a software module or control routine for the system, which in effect can provide a controllable model of the system. The processor can use information accessed from the database together with one or software modules executed in the processor to determine control parameters or values for different components of the systems, e.g., different treatment times, different doses, etc. Using input interfaces to receive control instructions and output interfaces linked to different system components in the system, the processor can perform active control over the system.

In certain configurations, the exact nuclear medication used with the devices, systems and methods described herein may vary. For example, lutetium-177-DOTATATE, lutetium-177-DOTATAC, yttrium-90-DOTATATE, or yttrium-90-DOTATAC can be used to treat neuroendocrine tumors. Strontium-189 chloride, samarium-153, radium-223 and radium-223 dichloride can be used to treat prostate cancer. Yttrium-90 ibritumomab tiuxetan and iodine-131 tositumomab can be used to treat indolent B-cell lymphoma. Yttrium-90 and iodine-131 can be used in tandem with monoclonal antibodies to treat non-Hodgkin's lymphoma. Samarium-153-EDTMP and strontium-89-chloride can be used for palliation of bone metastases. In other instances, a radionuclide material may comprise one or more of bromine-77, indium-111, iodine-123, and iodine-125, lutetium-177, holmium-166, rhenium-186, rhenium-188, copper-67, promethium-149, gold-199, technetium-99m, strontium-89, radium-223, gallium-68, thorium-227, actinium-225 and rhodium-105. Some of these radioisotopes can be used in imaging applications, whereas other radioisotopes, e.g., beta and alpha emitters, are typically used in targeted radionuclide therapy materials. The binding moiety used with the radionuclide may vary and can be based on heme rings, peptides, lipids or other groups that can bind specifically to a receptor on a cell. If desired, the nuclear medicine material can be packaged in a kit optionally with the substrate and/or the radiation measuring device.

In certain embodiments, the devices described herein can be used in monitoring infusion of a nuclear medication to a patient. For example, radiation levels of a nuclear medication passing through an intravenous line can be measured using the substrate and a radiation measuring device. For example, the device can be configured to receive and retain a radiation probe during infusion of a nuclear medication and can include a substrate comprising an aperture configured to receive and retain the radiation probe at a first surface of the substrate, wherein the substrate is configured to receive and retain the intravenous line at a second surface of the substrate. The aperture can be configured to position the received radiation probe to measure radiation levels of the nuclear medication passing through the received intravenous line during infusion of the nuclear medication. If desired, an alert can be generated, e.g., by the processor or by the radiation measuring device itself, when the measured radiation levels have reached a selected counts per hour. Treatment may then be discontinued.

In other embodiments, the devices described herein can be used in treating a patient using a nuclear medication. For example, the substrate and a radiation measuring device can be used to count radiation, e.g. counts per second, of the nuclear medication passing through an intravenous line connected to the patient. As noted herein, a device configured to receive and retain a radiation probe during infusion of a nuclear medication can be used. The device can include a substrate comprising an aperture configured to receive and retain the radiation probe at a first surface of the substrate, wherein the substrate is configured to receive and retain the intravenous line at a second surface of the substrate, and wherein the aperture is configured to position the received radiation probe to measure radiation levels of the nuclear medication passing through the received intravenous line during infusion of the nuclear medication. Once a selected counts per second or counts per hour are measured, the infusion of the nuclear medication can be discontinued. For example, a treating physician may specify or select a terminal rate based on the medication manufacturer's recommendation in treating a specific disease or disorder. If desired, an alert can be generated when the selected counts per hour of the radiation are measured or reached. This alert can be generated by the radiation measuring device or a processor or other system.

When introducing elements of the examples disclosed herein, the articles "a," "an," "the" and "said" are intended to mean that there are one or more of the elements. The terms "comprising," "including" and "having" are intended to be open-ended and mean that there may be additional elements other than the listed elements. It will be recognized by the person of ordinary skill in the art, given the benefit of this disclosure, that various components of the examples can be interchanged or substituted with various components in other examples.

Although certain aspects, configurations, examples and embodiments have been described above, it will be recognized by the person of ordinary skill in the art, given the benefit of this disclosure, that additions, substitutions, modifications, and alterations of the disclosed illustrative aspects, configurations, examples and embodiments are possible.

What is claimed is:

1. A device configured to receive and retain a radiation probe during administration of a nuclear medication to a subject, the device comprising a substrate comprising an aperture configured to receive and retain the radiation probe at a first surface of the substrate, wherein the substrate is configured to receive and retain a fluid line at a second surface of the substrate, wherein the substrate comprises a handle configured to receive and retain a reservoir comprising the nuclear medication to permit transport of the nuclear medication in the substrate, and wherein the aperture is configured to position the received radiation probe to measure radioactivity of the nuclear medication passing from the reservoir through the retained fluid line during administration of the nuclear medication to the subject.

2. The device of claim 1, wherein the aperture is sized and arranged to receive the radiation probe from a Geiger counter.

3. The device of claim 2, wherein the aperture is sized and arranged to receive and retain the entire radiation probe of the Geiger counter.

4. The device of claim 2, wherein the aperture is sized and arranged to receive and retain a head of the radiation probe of the Geiger counter.

5. The device of claim 1, wherein the second surface comprises a slot configured to receive and retain the fluid line.

6. The device of claim 5, wherein the slot is configured to position the received and retained fluid line transversely so the received and retained fluid line passes under a center of the received radiation probe.

7. The device of claim 1, wherein the substrate comprises a low Z material.

8. The device of claim 7, wherein the low Z material is one or more of an acrylic, a plastic, a rubber, wood, or a non-metallic material.

9. The device of claim 1, wherein the handle is circular shaped.

10. The device of claim 1, wherein the substrate comprises radiation absorbing particles.

11. A system for administering a nuclear medication to a subject, the system comprising:
   a radiation measurement device comprising a radiation probe; and
   a device configured to receive and retain the radiation probe during administration of the nuclear medication, the device comprising a substrate comprising an aperture configured to receive and retain the radiation probe at a first surface of the substrate, wherein the substrate is configured to receive and retain a fluid line at a second surface of the substrate, wherein the substrate comprises a handle configured to receive and retain a reservoir comprising the nuclear medication, and wherein the aperture is configured to position the received radiation probe to measure radioactivity of the nuclear medication passing through the received fluid line during administration of the nuclear medication.

12. The system of claim 11, wherein the radiation measurement device is a Geiger counter.

13. The system of claim 11, wherein the second surface comprises a slot configured to receive and retain the fluid line, wherein the slot is configured to position the received and retained fluid line transversely so the received and retained fluid line passes under a center of the received radiation probe.

14. The system of claim 11, wherein the substrate comprises a low Z material that is one or more of an acrylic, a plastic, a rubber, wood, or a non-metallic material.

15. The system of claim 11, wherein the aperture is sized and arranged to receive and retain a head of the radiation probe.

16. A method of administering a nuclear medication to a subject, the method comprising:
   placing a radiation probe in a device configured to receive and retain the radiation probe during administration of the nuclear medication, the device comprising a substrate comprising an aperture configured to receive and retain the radiation probe at a first surface of the substrate, wherein the substrate comprises a handle configured to receive and retain a reservoir comprising the nuclear medication;
   placing a fluid line at a second surface of the substrate, wherein the second surface of the substrate is configured to receive and retain the fluid line, and wherein the aperture is configured to position the received radiation probe to measure radioactivity of the nuclear medication passing from the reservoir and through the retained fluid line during administration of the nuclear medication to the subject.

17. The method of claim 16, further comprising configuring the second surface with a slot to receive and retain the fluid line.

18. The method of claim 16, further comprising configuring the aperture to receive and retain a head of the radiation probe of a Geiger counter.

19. The method of claim 16, further comprising configuring the substrate to shield a user from radiation as the radiation probe is placed into the aperture.

20. The method of claim 19, further comprising configuring the substrate with an acrylic material.

\* \* \* \* \*